United States Patent [19]

Buchler et al.

[11] Patent Number: 4,987,226

[45] Date of Patent: Jan. 22, 1991

[54] RHENIUM-OXO-PORPHYRIN COMPLEXES

[75] Inventors: Johann Buchler, Darmstadt; Steffen Kruppa, Neu-Isenburg; Manfred Schmidt, Gelnhausen, all of Fed. Rep. of Germany; Guenter Prescher, Larchmont, N.Y.

[73] Assignee: Degussa Aktiengesellschaft, Frankfurt am Main, Fed. Rep. of Germany

[21] Appl. No.: 555,672

[22] Filed: Jul. 18, 1990

Related U.S. Application Data

[63] Continuation of Ser. No. 247,299, Sep. 21, 1988, abandoned.

[30] Foreign Application Priority Data

Sep. 21, 1987 [DE] Fed. Rep. of Germany ....... 3731689

[51] Int. Cl.$^5$ ............................................. C07D 487/22
[52] U.S. Cl. ..................................... 540/145; 549/531
[58] Field of Search .......................................... 540/145

[56] References Cited

U.S. PATENT DOCUMENTS

| | | | |
|---|---|---|---|
| 3,778,451 | 12/1973 | Poite | 549/531 |
| 4,418,203 | 11/1983 | Kim | 549/531 |
| 4,822,899 | 4/1989 | Groves et al. | 549/533 |
| 4,845,252 | 7/1989 | Schmidt et al. | 549/531 |

OTHER PUBLICATIONS

Kruppa Dissertation, Technischen Hochschule Darmstadt 1989.

Sheldon, "Synthetic and Mechanical Aspects of Metal Catalyzed Epoxidations with Hydroperoxides", *Journal of Molecular Catalysis*, vol. 7, 1960, pp. 107–126.

Harriman et al., "Redox Reactions of Osmium Porphyrins", *Journal Chem. Soc.* Dalton Trans., 1988, pp. 2705–2711.

Hrung et al., "Salt-Type Complexes of Porphyrins:- Monocations Octaethylporphinium Tri-microhalogeno-hexacarbonyldirbenate (I)", *Journal of American Chemical Society*, vol. 98-24, Nov., 1976, pp. 7878–7880.

The Merck Index, 10th Edition, Martha Windholz, ed., (1983), entry numbers 8074 and 8077, p. 1180.

*Primary Examiner*—Richard L. Raymond
*Attorney, Agent, or Firm*—Beveridge, DeGrandi & Weilacher

[57] ABSTRACT

Rhenium-oxo complexes with
  octaethyl porphyrin or
  5,10,15,20-tetraphenyl porphyrins or
  5,10,15,20-tetra(4-pyridyl)-porphyrins as ligands
which optionally carry an anion on the central atom. Methods of preparing the complexes are also disclosed.

3 Claims, No Drawings

RHENIUM-OXO-PORPHYRIN COMPLEXES

This application is a continuation of U.S. patent application Ser. No. 07/247,299, filed Sept. 21, 1988, now abandoned.

INTRODUCTION AND BACKGROUND

The present invention relates to new transition metal complex compounds with
octaethyl porphyrin or
5,10,15,20-tetraphenyl porphyrins or
5,10,15,20-tetra(4-pyridyl)-porphyrins as ligands
which optionally carry an anion on the central atom and are suitable as catalysts for the epoxidation of olefins with hydrogen peroxide.

Olefin oxides (oxiranes) are compounds of considerable industrial significance. They are used in the area of varnishes, for the preparation of polyethers, polyurethanes, epoxide resins, detergents, glycols and a plurality of organic intermediate products (cf. U.S. Pat. No. 2,412,136 and DE-AS 11 39 477).

Various methods are already known for the epoxidation of olefins. Thus, oxiranes can be prepared according to the chlorohydrin method by reacting olefins with chlorine or sodium hypochlorite in alkaline medium and by a subsequent treatment with bases.

A further known process is based on the reaction of olefins with organic hydroperoxides in the presence of a catalyst (cf. DE-AS 14 68 012).

A further known method is based on the use of organic peracids obtained by oxidation in air of the corresponding aldehydes or from carboxylic acids with hydrogen peroxide (cf. BE-PS 535 068).

Disadvantages associated therewith can be eliminated by using hydrogen peroxide as epoxidation agent since in this instance, according to theory, only water should be formed along with the epoxidation product. Since the reactivity of hydrogen peroxide is weak in relation to olefins, epoxidations with this reagent are carried out with the use of catalysts. Catalysts such as molybdenum compounds and tungsten compounds are suitable only for a few olefins. The following developments are noted in this connection, for example, GB 837,464, in which the various metal catalysts described in "J.A.C.S.", vol. 59, pp. 2342 to 2344, 1937 are used; U.S. Pat. No. 2,786,854, according to which tungstic acid is used; U.S. Pat. No. 2,833 787, according to which acidic salts of metals of group VI of the periodic system of the elements, e.g. of tungsten or molybdenum, are used; BE-PS 860,776, according to which compounds containing tungsten and containing molybdenum are used; U.S. Pat. No. 3,993,673, according to which catalysts containing arsenic are used; U.S. Pat. No. 3,953,362, according to which a catalyst containing molybdenum is used; U.S. Pat. No. 4,026,908, according to which mercury derivatives plus a compound with molybdenum, tungsten, vanadium or titanium is used; U.S. Pat. No. 3,806,467, according to which organic and inorganic tin compounds plus organic or inorganic compounds containing molybdenum, tungsten, vanadium, selenium or boron are used; "Bull. Chem. Soc. Jap." 42, pp. 1604, 1969, according to which selenium dioxide is used: and U.S. Pat. No. 3,778,451, according to which compounds with molybdenum, tungsten, vanadium, niobium, tantalum, uranium and rhenium are used.

These substances are catalytically active; however, the methods which can fundamentally be carried out with them have not found acceptance in the art for various reasons. In conjunction with hydrogen peroxide solutions, either the hydrogen peroxide is rapidly decomposed by them or only an unsatisfactory epoxidation speed of reaction is achieved. Methods using these catalysts tend also to be problematical to the extent that in addition to the desired epoxidation product, frequently rather large amounts of byproducts such as diols and ketones are formed, the separation of which can pose considerable problems.

Attempts have also been undertaken in the past to carry out methods for the catalytic epoxidation of olefins with other epoxidation agents using metal porphyrin complexes as catalysts. Metal catalysts which have been suggested as suitable for reaction with epoxidation means such as iodosobenzene, alkali metal hypochlorite as well as organic hydroperoxides are e.g. chloro-iron-(III)-tetraphenyl porphyrin (FeCl) (TPP), chloro-manganese(III)-tetraphenyl porphyrin (MnCl) (TPP) or chloro-chromium(III)tetraphenyl porphyrin (CrCl) (TPP). Manganese(III)-tetraphenyl porphyrin has also already been used with hydrogen peroxide as oxidation agent (J.-P. Renaud; P. Battioni; J. F. Bartoli; D. Mansuy, "J. Chem. Soc., Chem. Commun.", 1985, 888). However, these catalysts exhibit a strong decomposing action on $H_2O_2$, so that the selectivities which can be achieved regarding hydrogen peroxide are only very low unless expensively substituted porphyrin ligands are used.

Oxo-metal porphyrin complexes such as oxo-chloro(5,10,15,20-tetraphenyl porphyrinato)-molybdenum (v) (O=Mo (TPP) Cl) have also already been suggested in combination with organic hydroperoxides. However, an attempt to use hydrogen peroxide with a catalyst of the composition methoxo-oxo(5,10,15,20-tetraphenyl porphyrin)-molybdenum(v) for epoxidizing the olefin cyclohexene instead of an organic hydroperoxide failed: No epoxidation was able to be observed (F. Varescon, Thesis, Claude Bernard University, Lyons I, 1982).

SUMMARY OF THE INVENTION

The subject matter of the present invention relates to new rhenium-oxo-complexes with
octaethyl porphyrin or
5,10,15,20-tetraphenyl porphyrins or
5,10,15,20-tetra(4-pyridyl)-porphyrins as ligands
which optionally carry an anion on the central atom, except $O/2-(\mu\text{-oxo})$, $CH_3O^-$, $C_6H_5O^-$ or $F^-$. These complexes are suitable for the catalytic epoxidation of olefins with hydrogen peroxide with very high selectivity.

The complexes can have $Cl^-$, $Br^-$, $I^-$, $C_2H_5O^-$, $t-C_4H_9O^-$, $AcO^-$, $SCN^-$, $OCN^-$, and $ClO_4^-$ as the anion.

In the parent substances, hydrogen atoms or free electron pairs can be substituted one or more times on the phenyl groups or pyridyl groups of the porphyrin ligands by halogen, hydroxy, carboxy, cyano, rhodano, nitro, $C_1-C_6$-alkyl, trihalogen methyl, $C_1-C_6$-alkoxy, $C_1-C_6$-alkane sulfonyloxy, aminocarbonyl, aminocarbonyl containing one or two $C_1-C_6$-alkyl groups, $C_1-C_6$-alkyl carbonyl, amino, di-$C_1-C_6$-alkyl amino, $C_1-C_6$-alkanoyl amino, $C_1-C_6$-alkyl-$C_1-C_6$-alkanoyl amino, $C_1-C_6$-alkane sulfonyl amino, $C_1-C_6$-alkyl-$C_1-C_6$-alkane sulfonyl amino, aminosulfonyl, aminosulfonyl containing one or two $C_1$-$C_6$-alkyl groups, $C_1$-$C_6$-alkoxysulfonyl ($-SO_2-O-C_1-C_6-$alkyl) sulfo or $C_1$-$C_6$-alkane sulfonyl and twice in o-position by the methylene dioxy group, and the anion can optionally be $Cl^-$, $Br^-$, $I^-$, $C_2H_5O^-$, t-$C_4H_9O^-$, $AcO^-$, $SCN^-$, $OCN^-$, and $ClO_4^-$ or also $O/2^-(\mu$-oxo), $CH_3O^-$, $C_6H_5O^-$ or $F^-$, which brings about any charge equalization which may be required.

In another aspect, the present invention relates to a method of preparing rhenium-oxo complexes, especially those that are described above, which is carried out by reacting one mole octaethyl porphyrin, 5,10,15,20-tetraphenyl porphyrin or 5,10,15,20-tetra(4-pyridyl)-porphyrin with at least one mole rhenium pentahalogenide and 1 mole water. A high-boiling solvent which dissolves all reactants is employed as the reaction medium. Temperatures of 160°-250°, preferably 180°-220° C., have been found to be suitable for the reaction.

After reaction, the solvent is removed, preferably in a vacuum, and the residue is fractioned after having been taken up in an organic solvent by column chromatography. Then, the complexes which are present in the main fraction and are still inhomogeneous as regards the composition of the anion can be reacted with an equimolar amount of an alkali metal compound which is optionally produced in situ and contains the desired anion in a bond with the alkali metal. Temperatures of 0°-100°, preferably 40°-60° C. are used and the treatment employs a solvent mixture which dissolves both the rhenium-oxo complex as well as the alkali metal compound. The resulting rhenium-oxo complexes carrying the desired anion are crystallized therefrom by concentration and evaporation.

Alternatively, the initial complexes can be treated with an excess of the Brönsted acid corresponding to the desired anion at 20°-180°, preferably 40°-120° C. in solvent mixtures which dissolve both the rhenium-oxo-halogen complex as well as the Brönsted acid. As in the first variation, the resulting rhenium-oxo complexes carrying the desired anion are crystallized therefrom by concentration and evaporation.

DETAILED DESCRIPTION OF THE INVENTION

The catalytic properties of the compounds of the invention can be controlled and optimized, adapted to the particular olefin, by means of the steric and electronic effects of the mentioned substituents on the phenyl group or pyridyl group of the 5,10,15,20-tetraphenyl porphyrin or 5,10,15,20-tetra-(4-pyridyl) porphyrin.

The catalysts of the present invention are new substances. A number of them are accessible in great purity according to the known methods in the literature: J. W. Buchler et al., "Chem. Ber.", 1973, 106, 2710; "Liebigs Ann. Chem.", 1971, 745, 135; "Inorg. Nucl. Chem. Lett.", 1972, 8, 1073; K. Rohbock, dissertation, RTWH Aachen, 1972; H. Stoppa, dissertation, RTWH Aachen, 1976.

The various porphyrin ligands are prepared, to the extent that they can not be purchased, according to Adler et al., "J. Org. Chem." 32, 476, 1967 and Adler et al., "J. Heterocycl. Chem." 5, 669, 1968 and freed, in so far as required, of chlorine (porphyrin with a partially hydrated pyrrole member) (K. M. Smith et al., "Tetrahedron Lett.", 30, 2887, 1973).

Oxorhenium(V)-porphyrins are obtained from $Re_2O_7$ in a phenol melt in a relatively protracted and complicated method (septivalent rhenium is reduced to pentavalent rhenium). Previously, only binuclear porphyrin derivatives of monovalent rhenium with carbon monoxide as further ligands were prepared; the latter have e.g. the composition $Re_2(CO)_6(TTP)$ (M. Tsutsui et al., "J. Am. Chem. Soc." 94, 7603, 1972; ibid. 98, 7878, 1976; ibid; 99, 620, 1977). The insertion of rhenium presented here via rhenium pentahalogenides, e.g. rhenium pentachloride, results in a smooth reaction without change of the oxidation stage in very good yields of rhenium porphyrins.

Another important subject of the invention is therefore a method of preparing rhenium-oxo-complexes in general and in particular, however, the new rhenium complexes of the invention. The method is characterized in that one mole octaethyl porphyrin, 5,10,15,20-tetraphenyl porphyrin or 5,10,15,20-tetra(4-pyridyl)-porphyrin is reacted with at least one mole rhenium pentahalogenide and 1 mole water in a high-boiling solvent which dissolves all reactants. Such high boiling solvents are well known in the art and any suitable one or mixture can be used. Reaction temperatures of 160°-250°, preferably 180°-220° C. are used. The solvent is removed, preferably in a vacuum, the residue fractionated after having been taken up in an organic solvent by column chromatography. Then the complexes which are present in the main fraction and are still inhomogeneous as regards the composition of the anion are then treated by either of two ways. In one variation the complex is reacted with an equimolar amount of an alkali metal compound which is optionally produced in situ and contains the desired anion in a bond with the alkali metal at 0°-100°, preferably 40°-60° C. in a solvent mixture which dissolves both the rhenium-oxo complex as well as the alkali metal compound. The rhenium-oxo complexes carrying the desired anion are thereafter crystallized therefrom by concentration and evaporation.

In the second of the two variations, the complex is treated with an excess of the Brönsted acid corresponding to the desired anion at 20°-180°, preferably 40°-120° C. in solvent mixtures which dissolve both the rhenium-oxo-halogen complex as well as the Brönsted acid. The rhenium-oxo complexes carrying the desired anion are crystallized therefrom by concentration and evaporation.

The reagent water mentioned in above in connection with the description of the method of the invention does not have to be added independently but rather penetrates during the insertion of rhenium in sufficient amount from the air or from the chemicals or vessel materials into the reagents so that dihalogeno-rhenium groups are hydrolysed to oxo-rhenium groups in the course of the reaction.

The reaction times for the insertion of rhenium into the particular initial porphyrin according to the methods of the invention are approximately in a range of 1 to 20 hours, usually around 2 hours.

The end point of the reaction can be determined spectrophotometrically. The UV/vis spectrum of the rheniumporphyrin formed appears instead of the UV/Vis spectrum of the initial porphyrin. A rough indication is furnished already by the dark green color of the solution of the final product.

Brönsted acids potentially suitable for unifying the composition of the anion are all compounds which contain the anions $Cl^-$, $Br^-$, $I^-$, $C_2H_5O^-$, $C_3H_7O^-$, $t-C_4H_9O^-$, $AcO^-$, $SCN^-$, $OCN^-$ and $ClO_4$. Also $F^-$, $O/2^-$, $OCH_3^-$ and $C_6H_5O^-$ are suitable, in combination with the proton.

Customary adsorbents such as aluminum oxides or silica gels are used in the column chromatography carried out according to the two preparation variants of the invention. A weakly polar solvent such as chloroform or toluene or a mixture of both is added as eluent for the separation of the non-reacted porphyrin and for the separation of the rhenium complex fraction (main fraction), a mixture of a weakly polar (e.g. chloroform or dichloromethane) and a strongly polar solvent (methanol, ethanol, propanol or acetone). A mixture of 50% by volume chloroform and 50% by volume methanol is particularly well-suited.

Very different olefins can be epoxidized with hydrogen peroxide with the new catalysts described. The work can be performed thereby in organic solvents, especially in those which permit a conversion of hydrogen peroxide from the aqueous phase into the organic phase.

The amounts of catalyst to be used can be within a wide range. The catalytic concentration to be used in the individual instance can be selected in accordance with the type of the selected rhenium-porphyrin compound provided as well as in accordance with the reactivity of the particular olefin to be reacted. Generally, the catalyst concentration range which 1/10000 to $\frac{1}{4}$ mole, preferably 1/5000 to 1/5 mole per mole hydrogen peroxide.

The catalysts which have been used can be recycled for reuse in further batches after suitable separation from the reaction mixture.

The reaction temperatures can be within a wide range. They depend on the particular activity of the catalyst used, the reactivity of the olefin used, the tendency of the desired oxirane to ring opening and the type of solvent. They are generally around 0° to 150°, preferably 20° to 120°, especially 20° to 80° C. The reaction times are normally around 10 minutes to 24 hours. The reactions can be carried out under atmospheric pressure or at higher pressures as long as the reaction system can be maintained in a liquid phase.

The olefin reaction is preferably performed within a pressure range between 1 and 50 bars.

The advantages which can be achieved with the invention are:
very short reaction times;
high selectivity (hardly any byproduct);
low catalytic concentration;
high chemical stability of the catalyst, especially in relation to the epoxidation agent;
no or only minimum $H_2O_2$ decomposition;
catalyst can be easily separated and reused.

The invention is explained in more detail in the following illustrative examples of embodiments for the individual methods of preparation.

The related application Ser. No. 07/247,300 filed Sept. 21, 1988 based on P 37 31 690.7-42 demonstrates the use of the rhenium-oxo complexes of the present invention as catalyst for olefin reactions.

The following examples 1-13 of various embodiments of the invention furnish complete instructions for the preparation of certain rhenium-oxo complexes. Examples 1-3 and 11 describe the combination of the introduction of rhenium and of the introduction of a defined anion into the complex. The remaining examples show the exchange of the axial ligands on the oxorhenium(V)-porphyrin.

Elementary analyses, UV-VIS-, IR and mass spectra serve to characterize the compounds. The position of the bands in the visible spectral range is very strongly influenced in the case of ReV porphyrins by the anion, which is in transposition to the oxo group.

A survey of the individual examples will be presented in advance.

The following applies to the structural formula and the numbering of the new rhenium complexes used in the examples:

| | | ReO(TTP)X | |
|---|---|---|---|
| No. | X | Remarks | No. R |
| 1 | O/2 | -oxo complex | a Me |
| 2 | OR | with R acc. to a-e | b Et |
| 3 | F | | c iPr |
| 4 | Cl | | d tBu |
| 5 | Br | | e Ac |
| 6 | I | | |
| 7 | OCN | | |
| 8 | NCS | | |
| 9 | OClO_3 | perchlorate | |

EXAMPLE 1

-oxobis[oxo{meso-tetra(p-tolyl)-porphyrinato}rhenium(V)], [ReO(TTP)]_2O (1)

1.1 Recovery from metal-free porphyrin

A solution of 1 g (1.5 mmole) $H_2(TTP)$ in 70 ml trichlorobenzene (TCB) was heated with 670 mg (2 mmoles) $ReCl_5$ to reflux. The course of the reaction was followed using the UV/VIS spectrum. After no more free porphyrin could be demonstrated in the spectrum after approximately 2 h, the TCB was removed in a vacuum and the residue freed in a high vacuum at 60° C. of the last traces of the TCB. The residue was chromatographed on $Al_2O_3$ (activity III, basic, 20×5 cm) with toluene/$CHCl_3$ (4:1). The green forerun, which was not identified further, was disposed of. The brownish-green main product was eluted with MeOH/$CH_2Cl_2$ (1:1) and the solvent removed in a vacuum. Then the matter was dissolved in 25 ml $CHCl_3$ under the addition of 2 ml 2 n KOH and agitated 12 h. The organic solvent was removed by gentle heating, the precipitated complex filtered off and washed to neutral with distilled water. Crystallization from toluene/$CH_2Cl_2$ yielded 1.11 g of (1)(83.9%) as bluish-green, scaly powder.

$C_{96}H_{72}N_8O_3Re$ (MW 1756.4)

Calculated: C 65.59; H 4.13; N 6.37; Found: C 65.71; H 4.22; N 6.29.

UV/VIS ($\lambda$max, log $\epsilon$):345.(4.94),462(5.29), 599(4.19),640(3.95) nm.

IR (KBr): 725 (Re—O), 670 cm$^{-1}$ (Re—O), typical for $\mu$-oxo bridge.

1.2 Preparation of 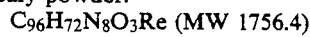 from ReO(TTP)Cl (4)

A solution of 200 mg ReO(TTP)Cl (0.21 mmole) in 25 ml $CHCl_3$ was agitated overnight with 10 ml 2 n KOH. Then the mixture was slightly warmed in order to evaporate the solvent, the precipitated complex filtered off and washed thoroughly to neutral with distilled water. After the product had been dried in a vacuum, crystallization from toluene yielded 141 mg (76.4%) bluish-green crystals which were spectroscopically identical to the product obtained in experiment 1.1.

EXAMPLE 2

Methoxo-oxo[meso-tetra(p-tolyl)-porphyrinato]rhenium(V), ReO (TTP)OMe (2a)

2.1 Recovery from metal-free porphyrin

A solution of 1 g (1.5 mmoles) H$_2$(TTP) in 70 ml trichlorobenzene (TCB) was compounded with 670 mg (2 mmoles) ReCl$_5$ and heated 2 h under reflux. The reaction was monitored UV/VIS-spectroscopically. After 2 h, no more free porphyrin was able to be demonstrated. The TCB was removed in a vacuum and the residue freed in a high vacuum at 60° C. of the last traces of the TCB and chromatographed on Al$_2$O$_3$ (activity III, neutral, 20×5 mc) with toluene/CHCl$_3$ (4:1). The green forerun, which was not investigated further, was disposed of and the brownish-green main fraction eluted with MeOH/CHCl$_3$ (1:1). After the removal of the solvent in a vacuum, the solution of the residue was compounded in CH$_2$Cl$_2$ with 100 ml MeOH and heated 4 h under reflux. The solvent was drawn off in a vacuum and the residue crystallized from MeOH/CH$_2$Cl$_2$. 1.28 g 2a (94.1%) was obtained in the form of a green, crystalline powder.

C$_{49}$H$_{39}$N$_4$O$_2$Re (MW 902.1)

Calculated: C 65.23, H 4.36, N 6.21, Found: C 65.07, H 4.11, N 6.08.

UV/VIS (λmax, logε):346(4.49),462(4.96), 588(4.04),656(3.86), 674(3.74) nm.

IR (KBr): 2790 (OCH$_3$), 9322 (Re≡O), 725 cm$^{-1}$ (Re—O)

MS: 902 (M+)

2.2 Recovery from ReO(TTP)Cl (4)

20 ml MeOH were added to a solution of 200 mg (0.22 mmole) ReO(TTP)Cl in 30 ml CHCl$_3$ and heated under reflux. The initially deep red solution began to turn green. After 4 hours, no free porphyrin was able to be demonstrated in the spectrum any longer with Uv/vIS spectroscopic analysis. The solvent was removed in a vacuum and crystallized from MeOH. 165 mg (81.8%) dark green crystals were obtained which exhibited, after drying in a vacuum, the same spectroscopic properties as the crystals obtained in experiment 2.1.

EXAMPLE 3

Chloro-oxo[meso-tetra(p-tolyl)-porphyrinato]rhenium(V), ReO (TTP)Cl (4)

3.1 Recovery from metal-free porphyrin

A solution of 1 g (1.5 mmoles) H$_2$(TTP) in 70 ml trichlorobenzene (TCB) was compounded with 670 mg (2 mmoles) ReCl$_5$ and heated 2 hours under reflux. Thereafter, no more free porphyrin was able to be demonstrated in the UV/VIS spectrum. The solvent was removed in a vacuum and the residue freed for 1 hour in a high vacuum at 60° C. of still-adhering TCB. The product was chromatographed on Al$_2$O$_3$ (activity III, neutral, 20×5 cm) with CHCl$_3$/toluene (4:1). The brownish forerun was not investigated further and was disposed of. The brownish-green main fraction was eluted with MeOH/CHCl$_3$ (1:1) and the solvent drawn off in a vacuum. Hydrochloric-acid gas predried with concentrated sulfuric acid was cautiously introduced into the solution of the residue in 250 ml toluene. After 10 min reflux boiling on a water separator, the initially dark green solution started to turn deep red. Approximately 2 hours later, the UV/VIS spectrum no longer changed. After removal of the solvent in a vacuum, 1.19 g of (4) (88.1%) in the form of reddish-black crystals was able to be obtained by crystallization from toluene.

C$_{48}$H$_{36}$N$_4$OReCl (MW 906.6)

Calculated: C 63.5, H 3.97, N 6.17. Found: C 63.40, H 4.09, N 5.85

UV/VIS (λmax, logε):338(4.70), 524(4.51), 654(4.02), 674(3.95) nm

IR (KBr): 970 (Re≡O), 725 cm$^{-1}$ (Re—O)

MS: 906 (M+)

3.2 Recovery from [ReO(TTP)]$_2$O (1)

A solution of 140 mg [ReO(TTP)]$_2$O (0.08 mmole) in 20 ml CHCl$_3$ was agitated overnight with 2 ml concentrated hydrochloric acid (37% by weight aqueous solution), the solvent evaporated and the residue washed neutral with distilled water. Crystallization from toluene at −15° C. yielded 117 mg of (4) (81.3%) reddish-black platelets which were spectroscopically identical to the material obtained in experiment 3.1.

EXAMPLE 4

Fluoro-oxo[meso-tetra(p-tolyl)-porphyrinato]rhenium(V), ReO(TTP)F (3)

4.1 Recovery from methoxide (2a)

A solution of 150 mg (0.17 mmole) ReO(TTP)OMe in 15 ml CH$_2$Cl$_2$ was compounded with 2 ml HF (40% aqueous solution). The mixture was allowed to evaporate under agitation and the residue was washed neutral with distilled water. Crystallization from toluene/CHCl$_3$ yielded 120 mg of (3) (78.9%) dark green, small scales.

C$_{48}$H$_{36}$N$_4$OReF (MW 890.1)

Calculated: C 64.71; H 4.04; N 6.29; Found: C 61.92; H 3.79; N 5.99 experiment 4.1. C 62.02 H 3.91N 6.03 experiment 4.2.

UV/VIS (λmax, logε):349(4.62), 476(4.93), 606(3.98), 652(3.84) nm

IR (KBr): 972 (Re≡O), 725(Re—O), 675 cm$^{-1}$ (Re-F)

MS: 890 (M+)

4.2 Recovery from [ReO(TTP)]$_2$O (1)

A solution of 140 mg (0.08 mmole) [ReO(TTP)]$_2$O in 20 ml CHCl$_3$ was compounded with 2 ml HF (40% by wt. aqueous solution) and agitated 24 h. The complex, which had been freed by heating of solvent and thoroughly washed neutral with distilled water, was crystallized from toluene. 120 ml (84.4% dark green, small scales of a material spectroscopically identical to (3) was obtained.

EXAMPLE 5

Bromo-oxo[meso-tetra(p-tolyl)-porphyrinato]rhenium(V), ReO(TTP)Br (5)

5.1 Recovery from methoxide (2a)

2 ml HBr (40% by wt. aqueous solution) was added dropwise to a solution of 200 mg (0.22 mmole) ReO(TTP)OMe in 20 ml CH$_2$Cl$_2$. The mixture was allowed to evaporate under careful heating and the filtered-off residue was washed neutral with distilled water.

Crystallization from toluene/CHCl$_3$ yielded 185 mg of (5) (83.5%) black crystalline powder.

C$_{48}$H$_{36}$N$_4$OReBr (MW 951)

Calculated: C 60.56; H 3.78; N 5.89. Found: C 60.68; H 3.79; N 5.72;

UV/VIS (max, log):346(4.83), 532(4.50), 666(3.75), 710(3.76) nm

IR (KBr): 975 (Re≡O), 727 cm$^{-1}$ (Re—O)
MS: 871 (ReO/TTP)+)

5.2 Recovery from [ReO(TTP)]$_2$O (1)

A solution of 140 mg (0.08 mmole) [ReO(TTP)]$_2$O in 25 ml CHCl$_3$ was compounded with 2 ml HBr (40% by wt. aqueous solution) and agitated under slight heating. After all the solvent had been evaporated, the residue was thoroughly washed to neutral with distilled water and crystallized from toluene. 132 mg of (5) (86.8%) was obtained as black crystalline powder which was spectroscopically identical to the powder obtained in experiment 5.1.

EXAMPLE 6

Iodo-oxo[meso-tetra(p-tolyl)-porphyrinato]rhenium(V), ReO(TTP)I (6)

6.1 Preparation from methoxide (2a)

A solution of 100 mg ReO(TTP)OMe in 10 ml CHCl$_3$ was compounded with 1 ml HI (57% by wt. solution in water).

The mixture was allowed to evaporate and the complex was washed to neutral with distilled water. In order to remove traces of free iodine, the complex was heated 1 day at 60° C. in a high vacuum. 72 mg of (6) (65.1%) in the form of dark green, shimmering crystals were obtained by crystallization from toluene/CHCl$_3$.

C$_{48}$H$_{36}$N$_4$OReI (MW 998)
Calculated: C 57.71; H 3.61; N 5.61;
Found: C 54.08; H 3.42; N 5.29. UV/VIS ($\lambda$max, log$\epsilon$):356(3.56), 492(4.42), 654(3.43) nm
IR (KBr): 967 (Re≡O), 727 cm$^{-1}$ (Re—O)
MS: no ions 6.2 Preparation from [ReO(TTP)]$_2$O (1)

A solution of 140 mg [ReO(TTP)]$_2$O (0.08 mmole) in 25 ml CHCl$_3$ was compounded with 2 ml HI (57% by wt. aqueous solution) and the solvent removed by means of cautious heating. The precipitated complex was washed neutral with distilled water and traces of free iodine were removed in a vacuum at 50° C. Crystallization from toluene yielded 112 mg of (6) (69.9%) dark green crystal platelets which were spectroscopically identical to the product obtained in experiment 6.1.

EXAMPLE 7

Cyanato-oxo[meso-tetra(p-tolyl)-porphyrinato]rhenium(V), ReO(TTP)OCN (7)

A solution of 200 mg ReO(TTP)Cl (0.22 mmole) in 200 ml CHCl$_3$ was compounded with approximately 100 mg KOCN and 5 drops glacial acetic acid. The mixture was allowed to evaporate under agitation and the filtered-off complex was thoroughly washed neutral with distilled water and dried 2 hours in a high vacuum at 60° C. Crystallization from toluene/CHCl$_3$ yielded 182 mg of (7) (90.5%) as deep green crystalline powder.

C$_{49}$H$_{36}$NO$_2$Re (MW 913.1)
Calculated: 64.39; H 3.94; N 7.67; Found: C 63.04; H 4.20; N 7.57.
UV/VIS ($\lambda$max, log$\epsilon$):340(4.61), 380(4.66), 512(4.46), 618(3.67) nm
IR (KBr): 2192 (N═C═O), 970 (Re≡O), 727 cm$^{-1}$ (Re—O)
MS: 913 (M+)

EXAMPLE 8

Thiocyanato-oxo[meso-tetra(p-tolyl)-porphyrinato]rhenium(V), ReO(TTP)NCS (8)

A solution of 150 mg ReO(TTP)Cl (0.16 mmole) in 20 ml CHCl$_3$ was compounded with one spatula tip KSCN and 5 drops glacial acetic acid. The mixture was agitated overnight under gentle heating and the precipitated complex washed neutral with distilled water. Then the complex was dried 1 day in a vacuum.

Crystallization from toluene/CHCl$_3$ yielded 135 mg of (8) (90.8%) as blackish-green crystalline powder.

C$_{49}$H$_{36}$N$_5$OReS (MW 929.9)
Calculated: C 63.28; H 3.87; N 7.531; Found: C 60.17; H 3.87; N 7.25.
UV/VIS ($\lambda$max, log$\epsilon$):334(4.71), 370(4.65), 520(4.54), 646(3.43) nm
IR (KBr): 2015 (N═C═S), 972 (Re≡O), 727 cm$^{-1}$ (Re—O)
MS: 929 (M+).

EXAMPLE 9

Perchlorato-oxo[meso-tetra(p-tolyl)-porphyrinato]rhenium(V), ReO(TTP)OClO$_3$ (9)

A solution of 120 mg [ReO(TTP)]$_2$O (0.06 mmole) in 10 ml CHCl$_3$ was compounded with 2 ml perchloric acid (7% by wt. aqueous solution). The mixture was slightly heated, the precipitated complex filtered off and washed to the neutral point with distilled water. After it was dried in a vacuum at 50° C., crystallization from toluene yielded 79 mg of (9) (76.5%) in the form of blackish-green crystalline powder.

C$_{49}$H$_{36}$N$_4$O$_5$ReCl (MW 970)
Calculated: C 59.3; H 3.71; N 5.77; Found: C 56.40; H 3.52; N 5.59.
UV/VIS ($\lambda$max, log$\epsilon$):326(4.65), 358(4.62), 500 (4.59), 624(3.70) nm
IR (KBr): 990 (Re≡O), 727 cm$^{-1}$ (Re—O)
MS: 970 (M+)

EXAMPLE 10

Ethoxo-oxo[meso-tetra(p-tolyl)-porphyrinato]rhenium(V), ReO(TTP)OEt (2b)

A solution of 200 mg (0.22 mmole) ReO(TTP)Cl in 10 ml CHCl$_3$ was compounded with approximately 50 mg NaOEt and heated with 20 ml EtOH for 4 hours under reflux. The solvent was removed in a vacuum and the complex was chromatographed on Al$_2$O$_3$ (activity III, neutral, 10×3 cm). Toluene/CHCl$_3$ (4:1) was used as mobile solvent and EtOH/CHCl$_3$ (1:1) served as eluent for the greenish-brown main product. After the solvent had been removed in a vacuum, the mixture was dissolved in EtOH, compounded with 5 drops HOAc and heated for 4 hours under reflux. The EtOH was drawn off in a vacuum and crystallization from EtOH performed. 152 mg of (2b) (75%) as green crystals were obtained.

C$_{50}$H$_{41}$N$_4$O$_2$Re (MW 916.1)
Calculated: C 65.50; H 4.47; N 6.11; Found: C 65.26; H 4.36; N 5.98.
UV/VIS ($\lambda$max, log$\epsilon$):336(4.41), 466(4.25), 504(4.19), 656(3.70) nm
IR (KBr): 950 (Re≡O), 727 cm$^{-1}$ (Re—O)
MS: 916 (M+)

EXAMPLE 11

Isopropyl-oxo[meso-tetra(p-tolyl)-porphyrinato]rhenium(V), ReO(TTP)OiPr (2c)

A solution of 335 mg (0.5 mmole) H$_2$(TTP) in 50 ml trichlorobenzene (TCB) was heated with 280 mg (0.75 mmole) ReCl$_5$ under reflux. After approximately 2 hours, no free porphyrin was able to be demonstrated any longer in the UV/VIS spectrum. After the solvent had been removed in a vacuum, the residue was freed for 1 hour in a high vacuum of the last remnants of TCB and chromatographed on Al$_2$O$_3$ (activity II, acidic, 10×3 cm) with toluene/CHCl$_3$ (4:1). The brownish-green forerun was disposed of, the green main product eluted with isopropanol/CHCl$_3$ (1:1) and the solvent drawn off in a vacuum. The solution of the residue in isopropanol was compounded with 5 drops glacial acetic acid and heated 4 hours under reflux. After the solvent had been drawn off in a vacuum, the complex was washed neutral with distilled water and crystallized from isopropanol. 297 mg of (2c) (64.1%) as green scales were obtained.

C$_{51}$H$_{43}$N$_4$O$_2$Re (MW 930.0)

Calculated: C 65.81; H 4.62; N 6.02; Found: C 65.39; H 4.48; N 6.07.

UV/VIS ($\lambda$max, log$\epsilon$):346(4.45), 464(4.73), 586(3.63) nm

IR (KBr): 935 (Re=O), 727 cm$^{-1}$ (Re—O)

MS: 930 (M+)

EXAMPLE 12

Tert-butyloxo-oxo[meso-tetra(p-tolyl)-porphyrinato]rhenium(V), ReO(TTP)Ot.Bu (2d)

A solution of 135 mg (0.15 mmole) ReO(TTP)Cl in 15 ml CHCl$_3$ was heated with 5 drops glacial acetic acid as well as 100 ml tert-butanol 4 hours until reflux. The solvent was removed in a vacuum and the residue washed to neutral with distilled water. Crystallization from tert-butanol yielded 122 mg of (2d) (86.7%) in the form of deep green crystalline platelets.

C$_{52}$H$_{45}$N$_4$O$_2$Re (MW 944.1)

Calculated: C 66.09; H 4.77; N 5.93; Found: C 65.61; H 4.66; N 5.85.

UV/VIS ($\lambda$max, log$\epsilon$):344(4.66), 458(4.89), 584(4.03), 654(3.95), 674(3.85) nm IR (KBr): 925 (Re=O), 670 cm$^{-1}$ (Re—O)

MS: 944 (M+)

EXAMPLE 13

Acetato-oxo[meso-tetra(p-tolyl)-porphyrinato]rhenium(V), ReO(TTP)OAc (2e)

A solution of 150 mg [ReO(TTP)]$_2$O (0.08 mmole) in 20 ml CHCl$_3$ was compounded with 1 ml glacial acetic acid and 50 mg NaOAc and freed of solvent under careful heating. The filtered-off complex was washed to neutral with distilled water and dried in a vacuum. Crystallization from toluene yielded 113 mg of (2e) (71.2%) as green crystalline powder.

C$_{50}$H$_{39}$N$_4$O$_3$Re (MW 929.8)

Calculated: C 64.53; H 4.19; N 6.02; Found C 64.78; H 4.29; N 5.92.

UV/VIS ($\lambda$max, log $\epsilon$):348(4.60), 418(4.29), 464(4.75), 602(3.83), 654(3.69) nm IR (KBr): 1670 (OAc, monodentate), 967 (Re=O), 727 cm$^{-1}$ (Re—O)

MS: 930 (M+)

Details of solvent removal technique, including use of vacuum, fractionation to obtain the desired complex using column chromatography and the like are set forth in the examples above and are conventional. Any suitable technique can be used. Similarly, crystallization techniques as shown in the examples are conventional.

Further variations and modifications of the foregoing will be apparent to those skilled in the art and are intended to be encompassed by the claims appended hereto.

We claim:

1. A rhenium(V)-oxo complex with
   octaethyl porphyrin or
   5,10,15,20-tetraphenyl porphyrins or
   5,10,15,20-tetra(4-pyridyl)-porphyrins as ligands,
wherein said ligands optionally carry an anion on the central atom; wherein the hydrogen atoms or free electron pairs of said ligands can be substituted once or several times on the phenyl, groups or pyridyl groups of the porphyrin ligands by halogen, hydroxy, carboxy, cyano, rhodano, nitro, C$_1$-C$_6$-alkyl, trihalogen methyl, C$_1$-C$_6$-alkoxy, C$_1$-C$_6$-alkane sulfonyloxy, aminocarbonyl, aminocarbonyl containing one or two C$_1$-C$_6$-alkyl groups, C$_1$-C$_6$-alkyl carbonyl, amino, di-C$_1$-C$_6$-alkyl amino, C$_1$-C$_6$-alkanoyl amino, C$_1$-C$_6$-alkyl-C$_1$-C$_6$-alkanoyl amino, C$_1$-C$_6$-alkane sulfonyl amino, C$_1$-C$_6$-alkyl-C$_1$-C$_6$-alkane sulfonyl amino, aminosulfonyl, aminosulfonyl containing one or two C$_1$-C$_6$-alkyl groups, C$_1$-C$_6$-alkoxysulfonyl (—SO$_2$—O—C$_1$-C$_6$—alkyl) sulfo or C$_1$-C$_6$-alkane sulfonyl and two of these groups can also be the methylene dioxy group, further provided that when the ligand is unsubstituted, the anion may not be F$^-$, 0/2$^-$ ($\mu$-oxo), CH$_3$O$^-$, or C$_6$H$_5$O$^-$.

2. Rhenium(V)-oxo complexes according to claim 1, wherein the ligand is unsubstituted and the anion is selected from the group consisting of Cl$^-$, Br$^-$, I$^-$, C$_2$H$_5$O$^-$, C$_3$H$_7$O$^-$, t—C$_4$H$_9$O$^-$, AcO$^-$, SCN$^-$, OCN$^-$, and ClO$_4^-$.

3. Rhenium(V)-oxo complexes according to claim 1, wherein the ligand is substituted and the anion is selected from the group consisting of Cl$^-$, Br$^-$, I$^-$, C$_2$H$_5$O$^-$, C$_3$H$_7$O$^-$, t—C$_4$H$_9$O$^-$, AcO$^-$, SCN$^-$, OCN$^-$, ClO$_4^-$, F$^-$, O/2$^-$ ($\mu$-oxo), CH$_3$O$^-$, and C$_6$H$_5$O$^-$.

* * * * *